(12) United States Patent
Crocker et al.

(10) Patent No.: US 6,521,642 B2
(45) Date of Patent: Feb. 18, 2003

(54) 5-CHLORO-3-(4-METHANESULFONYLPHENYL)-6'-METHYL-[2,3']BIPYRIDINYL IN PURE CRYSTALLINE FORM AND PROCESS FOR SYNTHESIS

(75) Inventors: Louis S. Crocker, Belle Mead, NJ (US); Ian W. Davies, Princeton, NJ (US); Richard G. Osifchin, Watchung, NJ (US); Andrew Kotliar, Hoboken, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/865,771

(22) Filed: May 25, 2001

(65) Prior Publication Data

US 2002/0016343 A1 Feb. 7, 2002

Related U.S. Application Data

(60) Provisional application No. 60/208,017, filed on May 26, 2000.

(51) Int. Cl.[7] .................. A61K 31/44; C07D 213/22
(52) U.S. Cl. ........................ 514/334; 546/257
(58) Field of Search ............................ 514/334; 546/257

(56) References Cited

U.S. PATENT DOCUMENTS

| | | | |
|---|---|---|---|
| 5,861,419 A | * 1/1999 | Dube et al. | 514/334 |
| 6,040,319 A | 3/2000 | Corley et al. | |
| 6,040,450 A | 3/2000 | Davies et al. | |
| 6,127,565 A | 10/2000 | Pye et al. | |
| 6,130,334 A | 10/2000 | Pye et al. | |
| 6,204,387 B1 | 3/2001 | Davies et al. | |
| 6,252,116 B1 | 6/2001 | Corley et al. | |

FOREIGN PATENT DOCUMENTS

| | | |
|---|---|---|
| WO | WO 98/03484 | 1/1998 |
| WO | WO 99/55830 | 11/1999 |
| WO | WO 01/37833 A1 | 5/2001 |

OTHER PUBLICATIONS

Schumacher Jr., et al., BMJ, Jun. 22, 2002, pp. 1488–1492, vol. 324.

Mealy, et al., Annual Review 2002: Drugs of the Future, pp. 403–434.

(List continued on next page.)

*Primary Examiner*—Alan L. Rotman
(74) *Attorney, Agent, or Firm*—Raynard Yurd; David L. Rose

(57) ABSTRACT

This invention encompasses the Form V polymorph of Compound A of structural formula:

Compound A

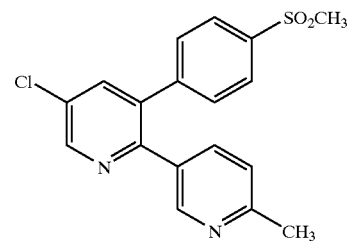

which is useful in the treatment of cyclooxygenase-2 mediated diseases. The invention encompasses certain pharmaceutical compositions for treatment of cyclooxygenase-2 mediated diseases comprising the Form V polymorph of Compound A. The invention also encompasses a process for synthesizing the Form V polymorph of Compound A.

14 Claims, 7 Drawing Sheets

OTHER PUBLICATIONS

Jackson Roberts II, et al., Goodman & Gilman's Pharmalogical Basis of Therapeutics, Chapter 27, pp. 687–731.

R.W. Friesen, et al., Bioorganic & Medicinal Chemistry Letters, (1998), vol. 8, No. 10, pp. 2777–2782.

Jean–Francois Marcoux, et al., J. Org. Chem., (2001), vol. 66, No. 12, pp. 4194–4199.

Ian W. Davies, et al., J. Org. Chem., (2000), vol. 65, No. 25, pp. 8415–8420.

Jean–Francois Marcoux, et al., Organic Letters, (2000), vol. 2, No. 15, pp. 2339–2341.

Ian W. Davies, et al., J. Org. Chem., (2000), vol. 65, No. 15, pp. 4571–4574.

* cited by examiner

5-CHLORO-3-(4-METHANESULFONYLPHENYL)-6'-METHYL-[2,3']BIPYRIDINYL IN PURE CRYSTALLINE FORM AND PROCESS FOR SYNTHESIS

CROSS-REFERENCE TO RELATED APPLICATIONS

This application claims the benefit of U.S. Provisional Application No. 60/208,017, filed on May 26, 2000.

BACKGROUND OF THE INVENTION

The present invention relates to the Form V polymorph of Compound A having the chemical structure shown below:

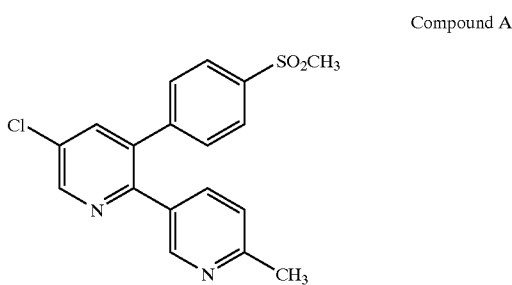

Compound A as well as a process for synthesizing the Form V polymorph.

Compound A exists in five polymorphic forms (Forms I–V), an amorphous form and two hydrated forms. The compound is a potent and selective cyclooxygenase-2 (COX-2) inhibitor, useful primarily in the treatment of inflammation, pain and fever as well as other COX-2 mediated diseases, such as described in PCT Publication Nos. WO96/10012 and WO96/16934. Compound A is described in U.S. Pat. No. 5,861,419 granted on Jan. 19, 1999 (Example 23), which is hereby incorporated by reference in its entirety. A process for making Compound A is described in U.S. Pat. No. 6,040,319 granted on Mar. 21, 2000, which is hereby incorporated by reference in its entirety. The present invention unexpectedly provides for a novel, robust process for making a Form V polymorph of compound A from any one of Forms I, II, III or IV or any mixture of polymorphs of compound A.

SUMMARY OF THE INVENTION

This invention encompasses the Form V polymorph of structural formula A:

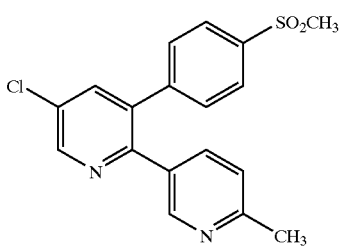

A which is useful in the treatment of cyclooxygenase-2 mediated diseases.

The invention encompasses certain pharmaceutical compositions for the treatment of cyclooxygenase-2 mediated diseases comprising the Form V polymorph of Compound A. The invention also encompasses a process for synthesizing the Form V polymorph of Compound A comprising: combining polymorph I, II, III or IV of Compound A with isopropyl acetate; heating to an elevated temperature less than about 75° C.; and cooling to a low temperature to produce the Form V polymorph.

BRIEF DESCRIPTION OF THE DRAWINGS

The invention is described in connection with the appended drawings in which.

DETAILED DESCRIPTION

Figure 1:
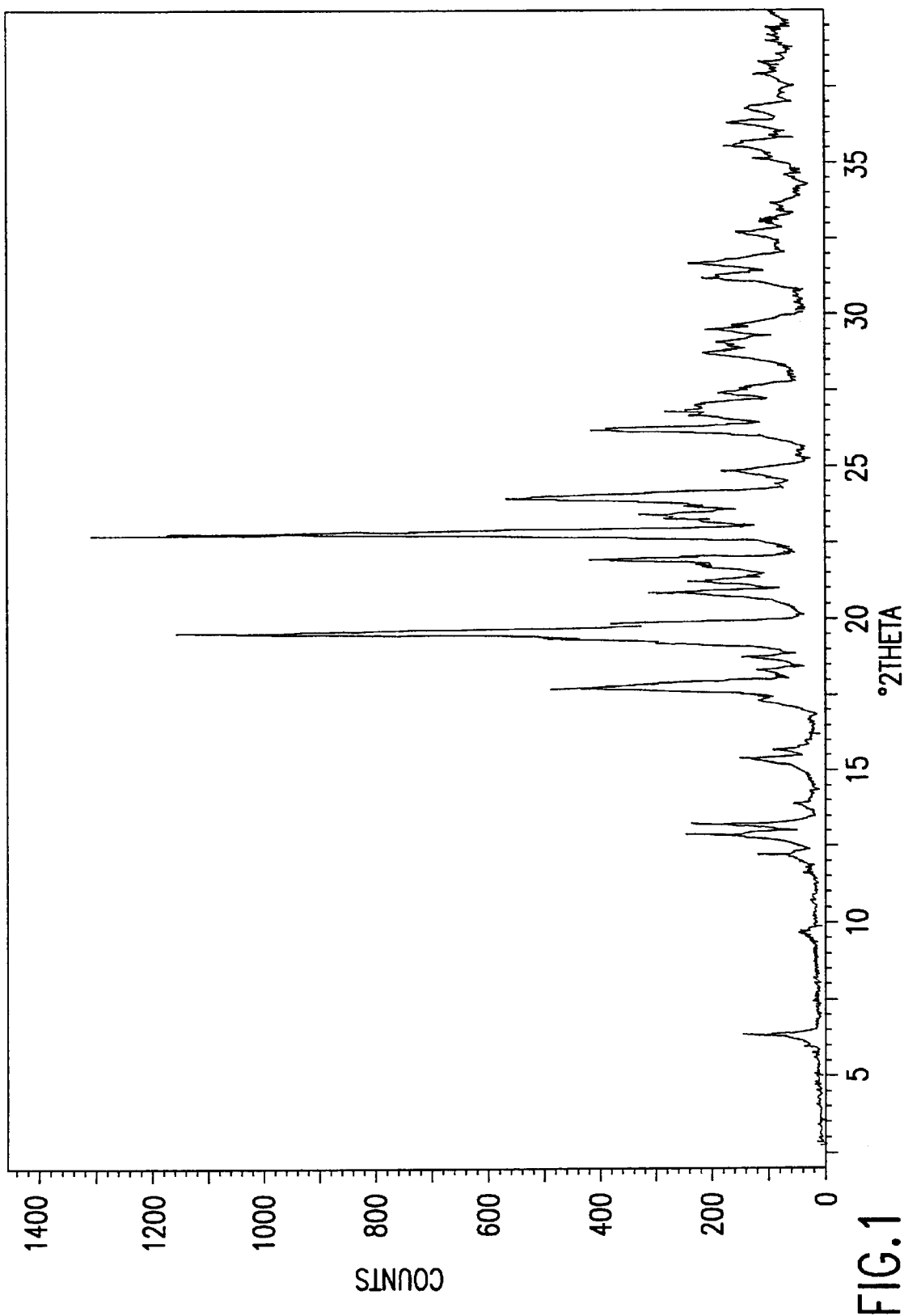
FIG. 1 is the X-ray powder diffraction (XRPD) pattern of Form V.
Figure 2:
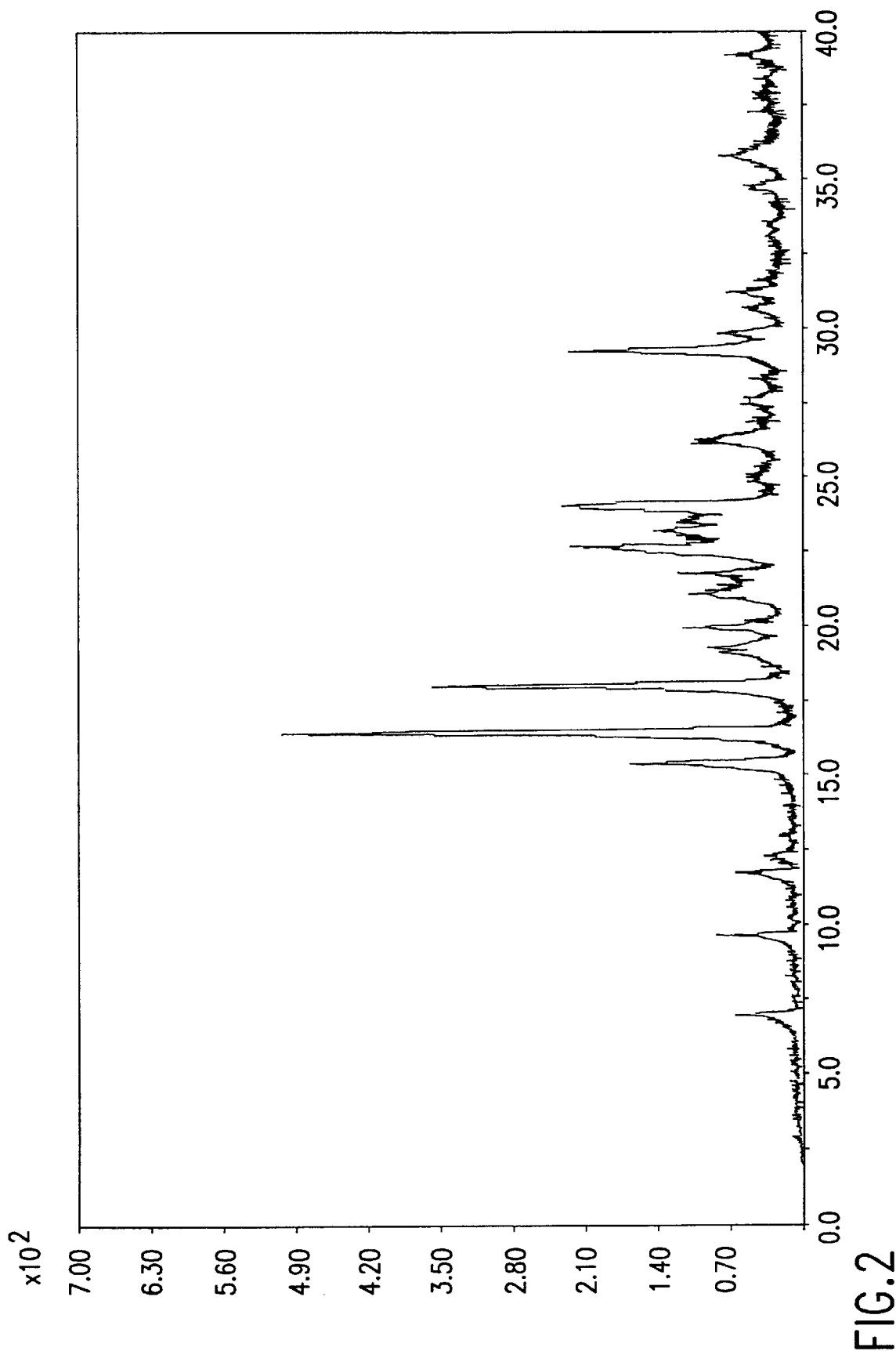
FIG. 2 is the XRPD pattern of Form I.
Figure 3:
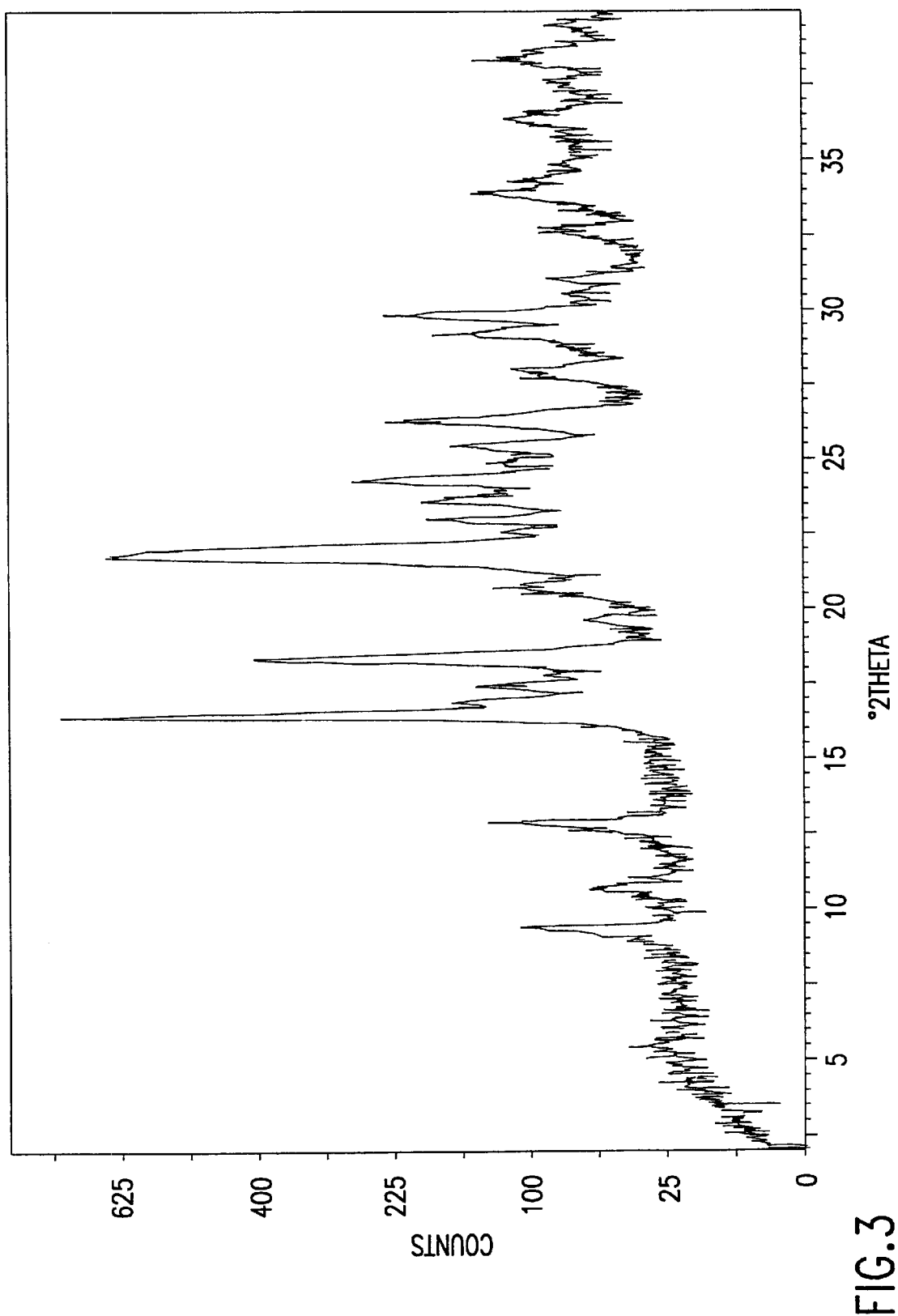
FIG. 3 is the XRPD pattern of Form II.
Figure 4:
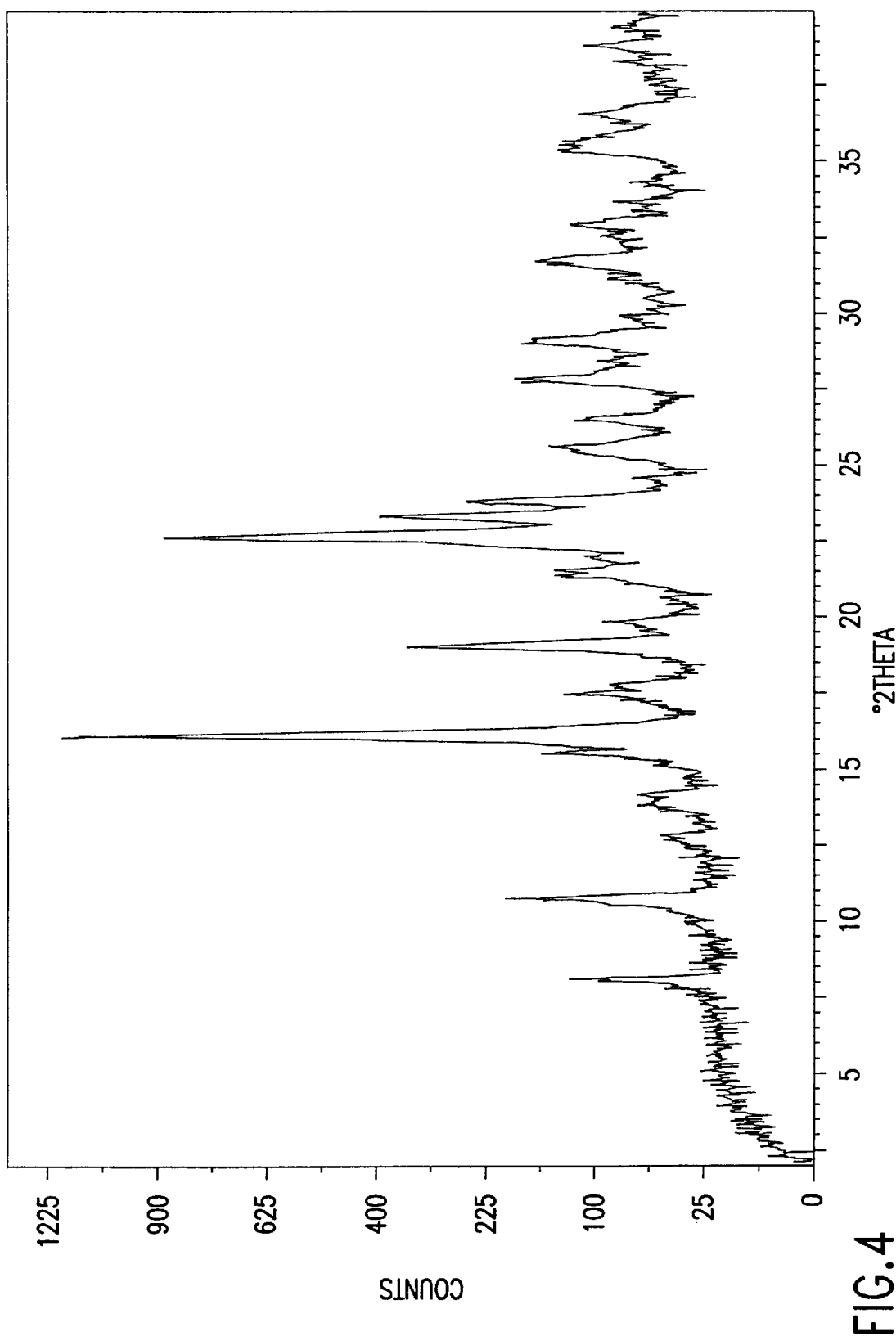
FIG. 4 is the XRPD pattern of Form III.
Figure 5:
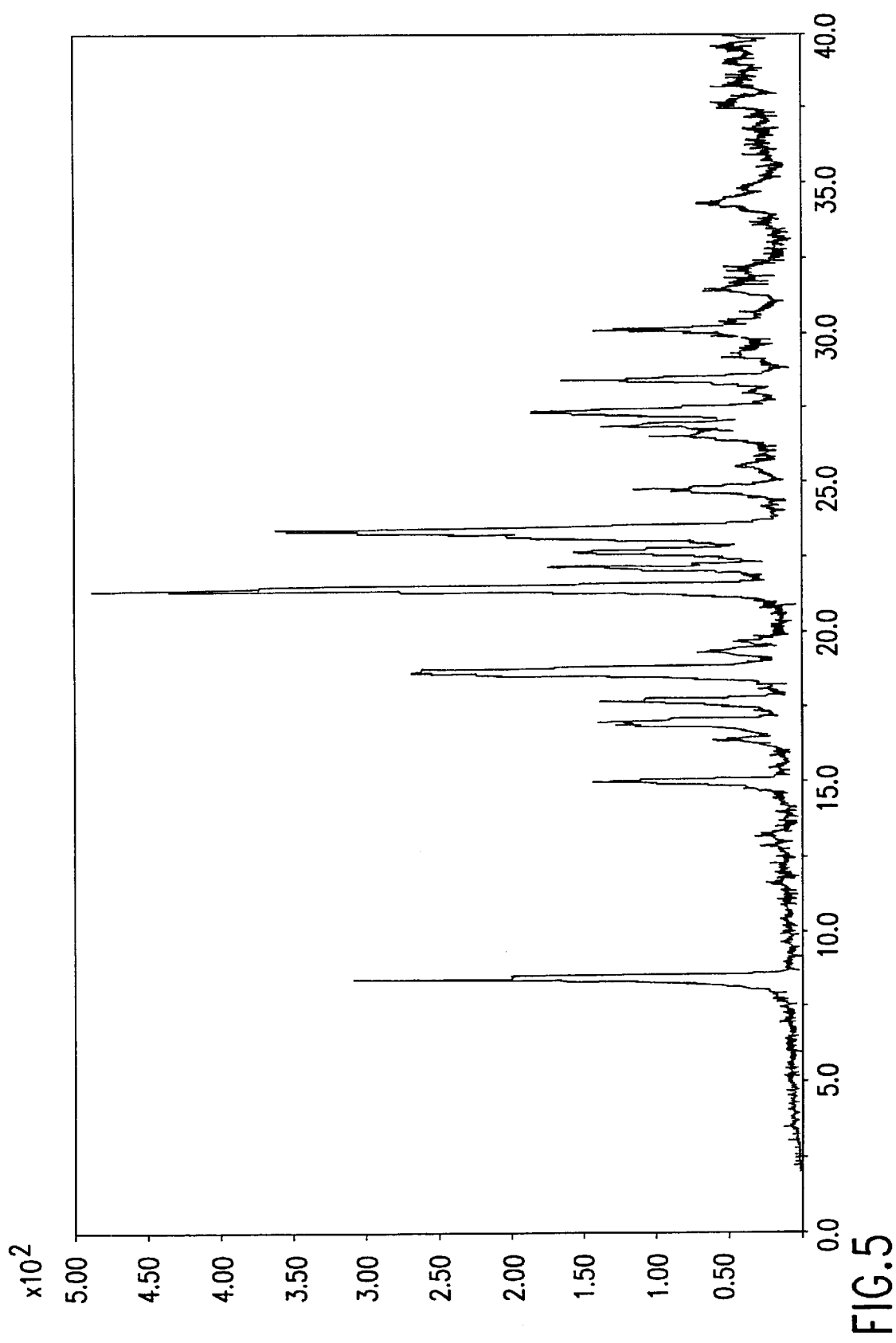
FIG. 5 is the XRPD pattern of Form IV.

This invention encompasses the Form V polymorph of structural formula A:

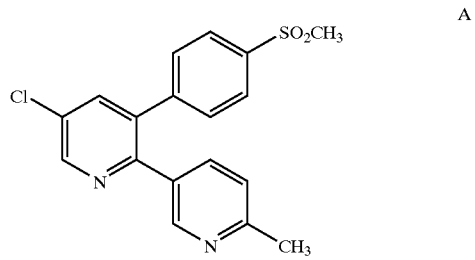

A having the following physical characteristics: DSC extrapolated onset melting temperature of 133.9° C., DSC peak melting temperature of 134.5° C., and x-ray powder diffraction peak positions, Cu K alpha, of: 13.7, 7.2, 6.9, 6.7, 5.8, 5.7, 5.0, 4.9, 4.8, 4.7, 4.5, 4.2, 4.0, 3.9, 3.8, 3.7, 3.6, 3.4, 3.3, 3.1, 3.0, 2.9 and 2.8 angstroms.

An embodiment of the invention is the Form V polymorph of Compound A characterized as having an x-ray powder diffraction pattern peak position, Cu K alpha, at about 13.7 angstroms. Within this embodiment of the invention is the Form V polymorph of Compound A further characterized as having at least one x-ray powder diffraction pattern peak position, Cu K alpha, at about, 7.2, 6.9, 6.7, 5.8, 5.7, 5.0, 4.9, 4.8, 4.7, 4.5, 4.2, 4.0, 3.9, 3.8, 3.7, 3.6, 3.4, 3.3, 3.1, 3.0, 2.9 or 2.8 angstroms.

An embodiment of the invention is the Form V polymorph of Compound A characterized as having a DSC extrapolated onset melting temperature of about 133.9° C.

An embodiment of the invention is the Form V polymorph of Compound A characterized as having a DSC peak melting temperature of about 134.5° C.

An embodiment of the invention is the Form V polymorph of Compound A having the aforesaid characteristics in substantially pure form.

The invention also encompasses a pharmaceutical composition comprising a non-toxic therapeutically effective amount of a Form V polymorph of Compound A and a pharmaceutically acceptable carrier.

An embodiment of the invention encompasses a method of treating an inflammatory disease susceptible to treatment with an non-steroidal anti-inflammatory agent comprising administering to a patient in need of such treatment a non-toxic therapeutically effective amount of a Form V polymorph of Compound A.

Another embodiment of the invention encompasses a method of treating a cyclooxygenase mediated disease advantageously treated by an active agent that selectively inhibits cyclooxygenase-2 in preference to cyclooxygenase-1 comprising administering to a patient in need of such treatment a non-toxic therapeutically effective amount of a Form V polymorph of Compound A.

Another embodiment of the invention encompasses a method for treating an illness selected from the group consisting of:
(a) rheumatic fever,
(b) symptoms associated with influenza or other viral infections, common cold,
(c) low back and neck pain,
(d) dysmenorrhea,
(e) headache,
(f) toothache,
(g) sprains and strains,
(h) myositis,
(i) neuralgia,
(j) synovitis,
(k) arthritis, including rheumatoid arthritis, degenerative joint diseases (osteoarthritis), gout and ankylosing spondylitis,
(l) bursitis,
(m) burns,
(n) injuries, and
(o) following surgical and dental procedures, comprising administering to a patient in need of such treatment a non-toxic therapeutically effective amount of a Form V polymorph of Compound A.

This invention also encompasses a novel process for making a Form V polymorph of structural formula A comprising: combining polymorph I, II, III or IV of Compound A with isopropyl acetate; heating to an elevated temperature less than about 75° C.; and cooling to a low temperature to produce the Form V polymorph.

For purposes of this Specification, the term 'elevated temperature' means any temperature above room temperature but less than about 75° C., as high as about 35–70° C., preferably about 50–65° C. Room temperature is about 20° C. The term 'low temperature' means any temperature below the 'elevated temperature', as low as about 0–30° C., preferably as low as about 10–20° C.

Polymorphic forms of Compound A, for purposes of this invention, are identified as Form I (onset of melting m.p. 135.7±0.2° C., peak m.p. 137.0±0.2° C.), Form II (onset of melting m.p 129.6° C., peak m.p. 131.5° C.), Form III (onset of melting m.p. 133.2° C., peak m.p. 134.4° C.), Form IV (onset of melting m.p. 133.72±0.04° C., peak m.p. 134.5±0.1° C.) and Form V (onset of melting, m.p. 133.9° C., peak m.p. 134.5° C.). Forms I through V are anhydrous.

An embodiment of the invention encompasses the process for making the Form V polymorph of Compound A which further comprises isolating the Form V polymorph. A subset of this embodiment encompasses isolating the Form V polymorph by filtration.

An embodiment of the invention is the process for making a Form V polymorph of Compound A wherein the elevated temperature is about 40–75° C. Another embodiment of the invention is the process for making a Form V polymorph of Compound A wherein the elevated temperature is about 50–65° C.

An embodiment of the invention is the process for making a Form V polymorph of Compound A wherein the low temperature is about 0–30° C. Another embodiment of the invention is the process for making a Form V polymorph of Compound A wherein the low temperature is about 10–20° C.

Another embodiment of the invention is the process for making a Form V polymorph of Compound A wherein the elevated temperature is about 50–65° C. and the low temperature is about 10–20° C.

The invention will now be illustrated by the following non-limiting examples:

Preparative Example A

The starting material Compound A was made in accordance with U.S. Pat. No. 6,040,319.

Preparative Example B

Form II

Form II was obtained by crystallizing Compound A obtained in accordance with Preparative Example A from ethyl acetate. Differential Scanning Calorimetry showed an extrapolated onset of melting at about 130° C., and a peak melting point of about 131° C.

Preparative Example C

Form IV

Form IV was prepared by mixing Preparative Example A (550.0 g, 1.54 mol) and toluene (4.0 L) and heating the mixture to 32.6° C. to cause dissolution. The solution was cooled to 16.5° C. and Form IV crystallized. The mixture was then cooled to 0° C. over 1 hr. n-Heptane (7.0L) was added over 2 hr and the mixture was filtered. The cake was washed with 3:1 n-heptane/toluene (3.0L) and dried to give the product (521.0 g) as a granular solid.

Preparative Example D

Hemihydrate

A solution of Preparative Example A (65 g) in 1 L of water wet toluene was heated to 60° C. and then cooled to ambient temperature. The hemihydrate form crystallized and was isolated by filtration. The solids were dried at ambient temperature under vacuum to give ~30 g of a colorless crystals.

Preparative Example E

Form III

The hemihydrate of Preparative Example D was heated to 90° C. in a vacuum oven for 12 hours and cooled down in the vacuum oven to give the Form III polymorph.

Preparative Example G

Amorphous

The amorphous form of compound A was obtained by heating the Form IV from Preparative Example C to above its melting temperature (above about 135° C.) under nitrogen, followed by quench cooling to room temperature under a dry atmosphere.

Preparative Example H

Mixture of Polymorphs

Compound 1 was synthesized in accordance with Preparative Example 1 of U. S. Pat. No. 6,040,319. Compound 2 was synthesized in accordance with Example 1 of U. S. Pat. No. 6,040,319.

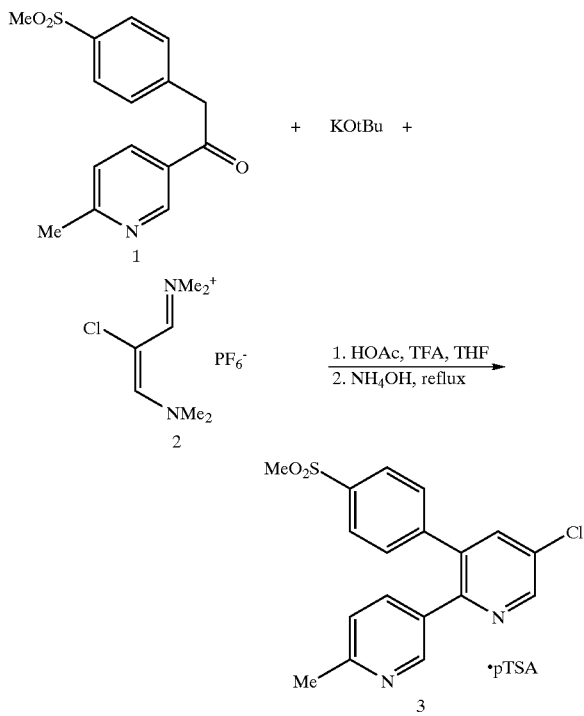

To a slurry of Compound 1 (1.10 kg) in tetrahydrofuran (THF) (2.5 L) at 0° C. was added potassium tert-butoxide (2.47 L). The resulting mixture was transferred to a slurry of Compound 2 (1.19 kg) in THF at ambient temperature. The slurry was transferred to a solution of acetic acid (1.5 L) and trifluoroacetic acid (TFA) (0.23 L) in THF. Concentrated ammonium hydroxide (1.50 L) was added and the mixture to reflux. The reaction mixture was cooled and the phases were cut. The THF layer was concentrated and toluene was added. The toluene layer was washed with aqueous sodium hydroxide followed by water and then concentrated to ~6 L. Acetone was added and a solution of p-toluenesulfonic acid (pTSA) (0.73 kg) in acetone was added and batch was filtered. The filter cake was washed with toluene/acetone and the solid dried in vacuo to give 1.80 kg of Compound 3 in ~90% isolated yield as an off white solid.

To a mixture of toluene, water and Compound 3 (1.80 kg) was added aqueous ammonia (1 equiv.). The phases were cut and the toluene layer was washed with water. The mixture was filtered through SOLKAFLOC and the filtrate was concentrated to a saturated solution and then cooled to ambient temperature and n-heptane was added. The solid was isolated by filtration, washed with toluene/n-heptane and then dried in vacuo to give Preparative Example H as an off-white solid.

EXAMPLE 1

FORM V OF 5-CHLORO-3-(4-METHANESULFONYLPHENYL)-6'-METHYL-[2, 3']BIPYRIDINYL

A mixture of Preparative Example H and isopropyl acetate (IPAC) was heated at 55° C. The suspension was cooled to ambient temperature and the solids were isolated by filtration. The solids were washed with IPAC and dried in vacuo to give the Form V polymorph (1.1 kg) as a colorless solid in 87% yield.

$^1$H NMR (400 MHz CDCl$_3$) δ8.69 (d, 1H, J=2.3 Hz), 8.36 (3, 1H, J=2.2 Hz), 7.88 (d, 2H, J=8.4 Hz), 7.72 (d, 1H, J=2.3 Hz), 7.54 (dd, 1H, J$_1$=8.0 Hz, J$_2$=2.3 Hz), 7.38 (d, 2H, J=8.5 Hz), 7.07 (d, 1H, J=8.0 Hz), 3.06 (s, 3H), 2.51 (s, 3H); $^{13}$C NMR (100 MHz CDCl$_3$) δ158.4, 152.2, 149.7, 148.3, 143.7, 140.1, 137.9, 137.2, 135.18. 131.1, 130.0, 130.3, 127.8, 122.7, 44.4, 24.1.

Characterization of Polymorphs

The polymorphic forms of compound A were characterized using the following procedures.

X-Ray Powder Diffraction Pattern Analysis

The X-ray patterns were collected using a Philips APD powder diffractometer utilizing copper K-alpha radiations. Table 1 below lists the XRPD peak locations for Forms I, II, III, IV and V as well as the hemihydrate and sesquihydrate forms. The peak positions are expressed in angstroms in Table 1.

TABLE 1

X-ray Powder Diffraction D-spacing for Crystalline Phases in Reflections (angstroms)

| Form I | Form II | Form III | Form IV | Form V | Hemi-hydrate | Sesqui-hydrate |
|---|---|---|---|---|---|---|
| 12.6 | 16.1 | 10.8 | 10.4 | 13.7 | 10.9 | 12.7 |
| 9.1 | 9.4 | 8.2 | 5.9 | 7.2 | 10.6 | 10.2 |
| 7.5 | 8.3 | 6.9 | 5.4 | 6.9 | 6.2 | 8.0 |
| 7.2 | 6.8 | 6.4 | 5.2 | 6.7 | 5.8 | 7.7 |
| 6.8 | 5.3 | 6.2 | 5.0 | 5.8 | 5.6 | 7.5 |
| 5.7 | 5.2 | 5.7 | 4.7 | 5.7 | 5.5 | 6.3 |
| 5.4 | 5.1 | 5.4 | 4.6 | 5.0 | 5.3 | 6.0 |
| 4.9 | 4.8 | 5.0 | 4.1 | 4.9 | 5.0 | 5.8 |
| 4.6 | 4.5 | 4.6 | 4.0 | 4.8 | 4.6 | 5.4 |
| 4.4 | 4.3 | 4.5 | 3.9 | 4.7 | 4.4 | 5.1 |
| 4.2 | 4.1 | 4.1 | 3.8 | 4.5 | 4.2 | 4.8 |
| 4.1 | 3.9 | 3.9 | 3.6 | 4.2 | 4.1 | 4.5 |
| 3.9 | 3.8 | 3.8 | 3.3 | 4.0 | 4.0 | 4.2 |
| 3.8 | 3.6 | 3.7 | 3.1 | 3.9 | 3.8 | 4.1 |
| 3.7 | 3.5 | 3.5 | 3.0 | 3.8 | 3.6 | 4.0 |
| 3.4 | 3.4 | 3.3 | | 3.7 | 3.4 | 3.9 |
| 3.1 | 3.2 | 3.2 | | 3.6 | 3.2 | 3.7 |
| | 3.0 | 3.1 | | 3.4 | 3.1 | 3.5 |
| | | 2.8 | | 3.3 | | 3.4 |
| | | | | 3.1 | | 3.3 |

TABLE 1-continued

X-ray Powder Diffraction D-spacing for
Crystalline Phases in Reflections (angstroms)

| Form I | Form II | Form III | Form IV | Form V | Hemi-hydrate | Sesqui-hydrate |
|--------|---------|----------|---------|--------|--------------|----------------|
|        |         |          |         | 3.0    |              | 3.1            |
|        |         |          |         | 2.9    |              |                |
|        |         |          |         | 2.8    |              |                |

Figure 6:
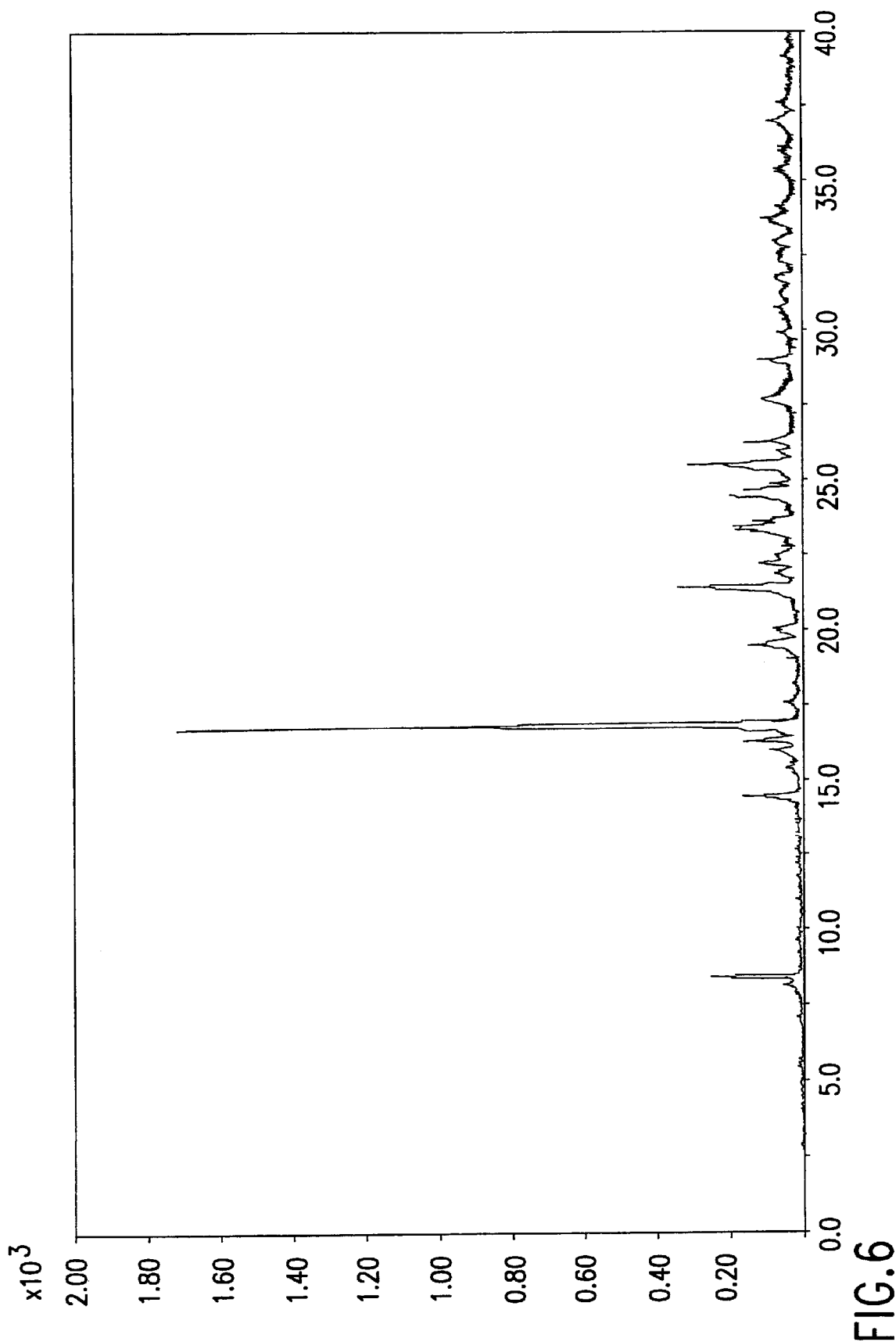
FIG. 6 is the XRPD pattern of the hemihydrate.
Figure 7:
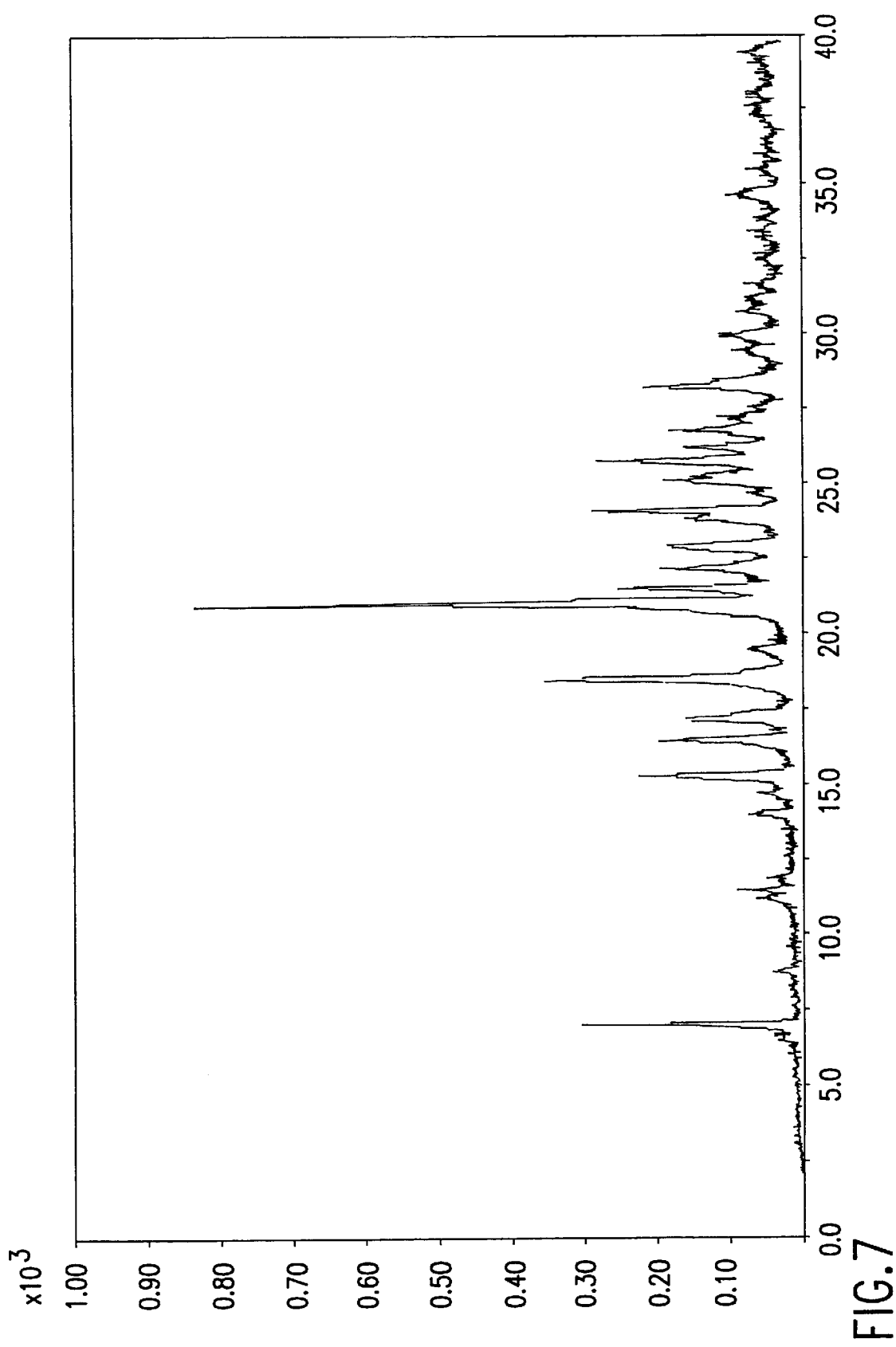
FIG. 7 is the XRPD pattern of the sesquihydrate.

The XPRD pattern for Form V is shown in FIG. 1. XRPD patterns for Forms I–IV are shown in FIGS. 2–5. XRPD patterns for the two hydrate forms are shown in FIGS. 6 and 7. The peak positions are expressed in degrees (2 theta) in the plots.

Differential Scanning Calorimetry (DSC)

DSC was carried out using a TA Instruments DSC 2910 instrument at a heating rate of 1° C./min under a nitrogen atmosphere in an open pan. The extrapolated onset temperatures, $T_o$, and enthalpy of fusion, $\Delta H$, observed for the melting endotherms are shown in Table 2 for Forms I, II, III, IV and V.

TABLE 2

Extrapolated melting temperature onset, $T_0$, and Enthalpy of Fusion obtained by DSC at 1° C./min in an open pan under nitrogen

| Polymorphic form | $T_0$(° C.) | Enthalpy of fusion, J/g |
|------------------|-------------|-------------------------|
| Form I           | 135.7 ± 0.2 | 72.9 ± 2.0              |
| Form II          | 129.6       |                         |
| Form III         | 133.2       |                         |
| Form IV          | 133.72 ± 0.04 | 76.9 ± 1.4            |
| Form V           | 133.9       | 84.8                    |

What is claimed is:

1. A polymorphic form of the compound of formula A:

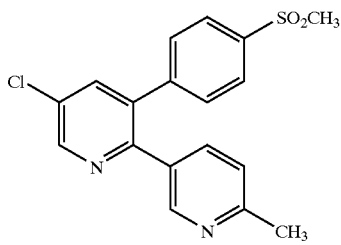

which is designated Form V, wherein the polymorphic form designated Form V has a d-spacing determined by x-ray powder diffraction, Cu K alpha, of about 13.7 angstroms.

2. A polymorphic form of the compound of formula A:

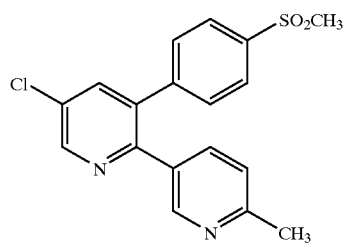

which is designated Form V, wherein the polymorphic form designated Form V has a d-spacing determined by x-ray powder diffraction, Cu K alpha, of about 13.7 angstroms, and wherein the polymorphic form designated Form V has at least one additional d-spacing determined by x-ray powder diffraction, Cu K alpha, of about: 7.2, 6.9, 6.7, 5.8, 5.7, 5.0, 4.9, 4.8, 4.7, 4.5, 4.2, 4.0, 3.9, 3.8, 3.7, 3.6, 3.4, 3.3, 3.1, 3.0, 2.9 or 2.8 angstroms.

3. A polymorphic form of the compound of formula A:

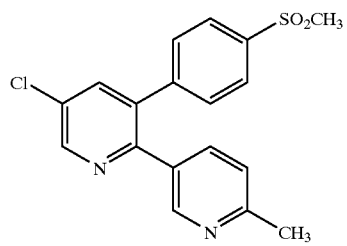

which is designated Form V, wherein the polymorphic form designated Form V has a Differential Scanning Calorimetry (DSC) extrapolated onset melting temperature of about 133.9° C.

4. A polymorphic form of the compound of formula A.

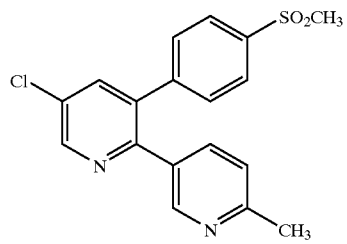

which is designated Form V, wherein the polymorphic form designated Form V has a Differential Scanning Calorimetry (DSC) peak melting temperature of about 134.5° C.

5. The polymorphic form according to claim 1 in substantially pure form.

6. A pharmaceutical composition comprising a non-toxic therapeutically effective amount of a polymorphic form according to claim 1 and a pharmaceutically acceptable carrier.

7. A method of treating an inflammatory disease susceptible to treatment with an non-steroidal antiinflammatory agent comprising administering to a patient in need of such treatment non-toxic therapeutically effective amount of a polymorphic form according to claim 1.

8. A method of treating a cyclooxygenase mediated disease advantageously treated by an active agent that selectively inhibits cyclooxygenase-2 in preference to cyclooxygenase-1 comprising administering to a patient in need of such treatment a non-toxic therapeutically effective amount of a polymorphic form according to claim 1.

9. A method for treating pain associated with the following conditions:

(1) low back and neck pain;

(2) headache;

(3) toothache;

(4) sprains and strains;

(5) bums;

(6) injuries; and (7) pain following surgical and dental procedures, comprising administering to a patient in need of such treatment a non-toxic therapeutically effective amount of a polymorphic form according to claim 1.

10. A method for treating dysmenorrhea comprising administering, to a patient in need of such treatment a non-toxic therapeutically effective amount of a polymorphic form according to claim 1.

11. A method for treating rheumatoid arthritis comprising administering a patient in need of such treatment a non-toxic therapeutically effective amount of a polymorphic form according to claim 1.

12. A method for treating osteoarthritis comprising administering to a patient in need of such treatment a non-toxic therapeutically effective amount of a polymorphic form according to claim 1.

13. A method for treating gout comprising administering to a patient in need of such treatment a non-toxic therapeutically effective amount of a polymorphic form according to claim 1.

14. A method for treating ankylosing spondylitis comprising administering to a patient in need of such treatment a non-toxic therapeutically effective amount of a polymorphic form according to claim 1.

* * * * *